United States Patent [19]

Stern

[11] 4,374,926

[45] Feb. 22, 1983

[54] METHOD FOR THE PRODUCTION OF IMPROVED CHYMOPAPAIN

[75] Inventor: Ivan J. Stern, Chicago, Ill.

[73] Assignee: Smith Laboratories, Inc., Northbrook, Ill.

[21] Appl. No.: 263,196

[22] Filed: May 13, 1981

[51] Int. Cl.$^3$ .......................... C12Q 1/38; C12N 9/50
[52] U.S. Cl. ..................................... 435/23; 435/219; 435/815
[58] Field of Search ................... 435/23, 24, 219, 815

[56] References Cited

U.S. PATENT DOCUMENTS

| | | | |
|---|---|---|---|
| 2,313,875 | 3/1943 | Jansen et al. | 435/219 |
| 3,248,300 | 4/1966 | Burdick | 435/219 |
| 3,274,072 | 9/1966 | Burdick | 435/219 |
| 3,284,316 | 11/1966 | Cayle | 435/219 |
| 3,320,131 | 5/1967 | Smith | 167/73 |
| 3,558,433 | 1/1977 | Stern | 435/219 |
| 4,039,682 | 8/1977 | Ausman et al. | 424/319 |

FOREIGN PATENT DOCUMENTS 7322964  1/1978  France .
1512491  6/1978  United Kingdom .

OTHER PUBLICATIONS

McCluskey & Thomas, The Removal of Cartilage Matrix, In Vivo, by Papain, 108 *J. Exp. Med.*, 371–382 (1958).
Potter et al., The Removal of Cartilage Matrix by Papain, 112 *J. Exp. Med.*, 1173–1194 (1960).
Hirsch, Studies on the Pathology of Low Back Pain, 41B, *J. Bone Jt. Surg.*, 237–243 (1959).
Mitchell et al., The Chemical Background of Intervertebral Disc Prolapse, 43B *J. Bone Jt. Surg.*, 141–151 (1961).
Harris & McNab, Structural Changes in the Lumbar Intervertebral Disc, 36B *J. Bone Jt. Surg.*, 304 (1954).
Feffer, Treatment of Low-Back and Sciatic Pain by the Injection of Hydrocortisone into Degenerated Intervertebral Discs, 38A *J. Bone Jt. Surg.*, 585 (1956).
Davidson et al., Biochemical Alterations in Herniated Disks, 234 *J. Bio. Chem.* 2951–2954 (1959).
Ebata & Yasunobu, Chymopapain, 237 *J. Biol. Chem.* 1086–1094 (1962).
Smith et al., Enzyme Dissolution of the Nucleus Pulposus in Humans, *Nature*, vol. 198 1311 (1963).
Jansen and Balls, *J. Biol. Chem.*, vol. 137 459 (1941).
The Merck Index, Ninth Edition, Entry No. 2261, p. 293.
Kunimitsu and Yasunobu, *Biochim. Biophys. Acta*, vol. 139, pp. 405–417 (1967).
Cayle and Lopez-Ramos, Abstracts of Papers of the 140th Meeting of the Am. Chem. Soc'y., Chicago, p. 19C (1961).
F. Mukai et al., *Biochim Biophys, Res. Comm.* 39, 983–988 (1970).
Shapiro, *Mutation Research*, vol. 39, 149–176 (1977).
Sussmuth et al., *Mutation Research*, vol. 40, 229–236 (1976).
Erlanger, *Arch. Biochem Biophys.*, 95, 271–278 (1961).
Baines et al., *J. Biochem* 177, 541–548 (1979).

*Primary Examiner*—Lionel M. Shapiro
*Attorney, Agent, or Firm*—Neuman, Williams, Anderson & Olson

[57] ABSTRACT

A method of preparing a purified proteolytically active chymopapain from crude chymopapain extracts by the use of exchange resin absorption purification techniques is provided. The purified chymopapain is characterized by relative freedom from proteolytically inactive, colored and/or toxic components and by its failure to form a precipitate with barium chloride test solution (U.S.P.) under acid conditions.

20 Claims, 1 Drawing Figure

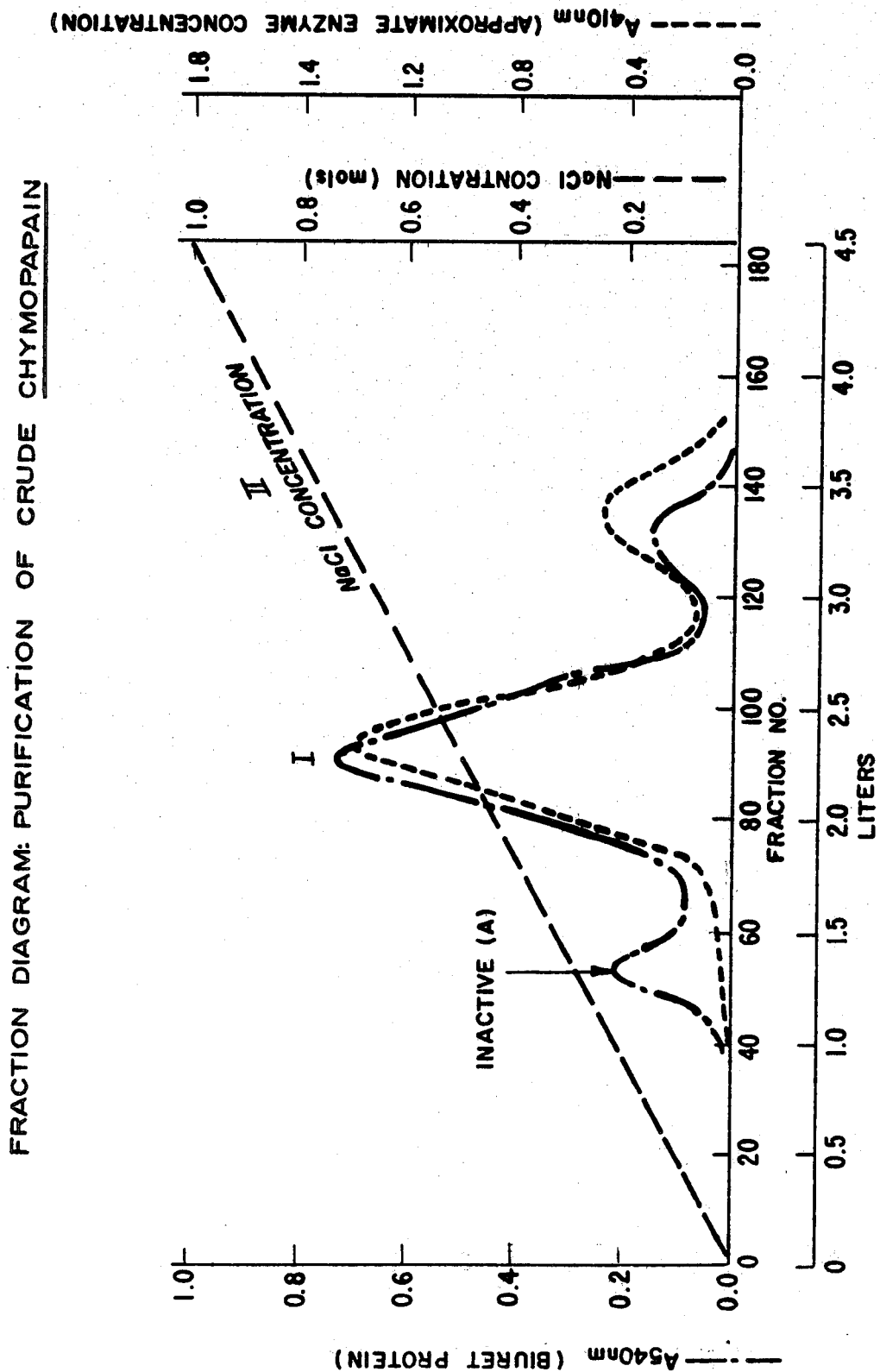

METHOD FOR THE PRODUCTION OF IMPROVED CHYMOPAPAIN

FIELD OF THE INVENTION

This invention relates to an improved chymopapain, and a method of producing the same.

DESCRIPTION OF THE PRIOR ART

Chymopapain is an enzyme which is the major proteolytic component of the crude latex of *Carica papaya*, caricaceae. It is characterized as a sulfhydryl enzyme similar to papain, but differs in respect to substrate specificities, electrophoretic mobility, stability, and solubility. It was first characterized and described by Jansen and Balls, J. Biol. Chem., vol. 137, pp. 459-60 (1941) and in U.S. Pat. No. 2,313,875 (1943). See The Merck Index, Ninth Edition, Entry No. 2261, p. 293.

The Jansen and Balls method for the preparation of chymopapain is essentially a salting-out procedure which consists of acidifying a solution of the soluble portion of the latex of papaya to a pH of about 2, separating the insoluble protein fraction from the liquid phase, raising the pH to 4, removing more protein, and then saturating the retained liquid phase with sodium chloride, then reducing the pH to about 2 to precipitate chymopapain.

Other researchers in the field have reported that the Jansen and Balls procedure when applied to a commercial papaya latex does not produce a single crystalline protein as described therein. See for example, Cayle and Lopez-Ramos, Abstracts of Papers of the 140th Meeting of the Am. Chem. Soc'y, Chicago, p. 19C (1961); Ebata and Yasunobu, J. Biol. Chem., vol. 237, pp. 1086-94 (1962); Kunimitsu and Yasunobu, Biochim. Biophys. Acta, vol. 139, pp. 405-17 (1967). Chymopapain separated from papaya by salt fractionation, and/or sovlent fractionation, and/or pH adjustment or by the use of similar methods is hereinafter referred to as crude chymopapain. Crude chymopapain has a distinct "sulfurous" odor as well as a pronounced yellow-brown color in solution.

Crude chymopapain in fact contains a variety of materials of a proteinaceous nature, of which only two are consistently active proteolytic factors. For example, in Stern, U.S. Pat. No. 3,558,433, patented Jan. 26, 1971 a method is described for purifying crude chymopapain. That patent identifies three components in crude chymopapain, namely two active proteolytic fractions known as chymopapain I and II and a proteolytically inactive proteinaceous component.

The procedure of U.S. Pat. No. 3,558,433 specified the use of a chromatographic column of carboxymethyl substituted cross-linked dextran copolymer previously equilibrated with an aqueous buffer solution and a pH of about 8 to about 8.5 to which the crude chymopapain was applied and then eluted by passing an aqueous buffer of the solution through a column having the same pH, but a greater ionic strength than the buffer solution used for equilibrating of the chromatographic column in the first instance.

More recently it has been found that the first fraction of chymopapain eluted from the chromatographic column by the Stern patent pocedure described as proteolytically "inactive", is in the case of some papaya extracts prepared by newer methods i.e. Baines et al, Biochem. J. 177, 541-48 (1979), actually proteolytically active. Thus, depending on the source of the raw material, an uncontrolled variability may be present in the composition of crude chymopapain.

The Stern patent identifies various components of chymopapain eluent by the absorption peak eluent maxima in FIG. 1 of the drawings, which were combined, dialyzed against distilled water and lyophilized.

SUMMARY OF THE INVENTION

In one broad form the present invention is a process for producing a purified chymopapain which comprises:

(a) contacting an aqueous buffered solution of crude chymopapain with a weakly acidic cationic exchanger comprising a column of carboxymethyl substituted cross-linked agarose gel, said "cationic exchanger" having been previously equilibrated with aqueous buffer solution having a pH of between about 6.5 and 7.5 and having a neutralizing capacity of from 0.02 to 0.1 milliequivalents of sodium hydroxide per cubic centimeter (cc.);

(b) eluting the chymopapain retained on the exchanger with an aqueous buffer solution having a pH in the same pH range as the buffer used for equilibrating the carboxymethyl substituted agarose gel, but having a linearly increasing ionic concentration of a compatible, non-reactive, water-soluble, pharmaceutically acceptable, neutral, inorganic salt with respect to eluent volume;

(c) collecting and discarding a first series of fractions of eluent from said exchanger containing an initially eluted colored and odoriferous protein component from crude chymopapain until the molarity of the eluent with respect to said soluble salt increases to and reaches the range of 0.25 to 0.4;

(d) continuously collecting and retaining a further series of fractions of chymopapain eluted from the exchanger comprising two proteolytically active chymopapain fractions at soluble salt concentrations greater than about 0.25 to 0.4 molar, until substantially all of the said absorbed chymopapain is recovered;

(e) recombining active fractions from step (d) and treating said retained fractions containing proteolytically active components of the chymopapain to remove the dissolved ionic inorganic salts and buffer components, and (f) lyophilizing the essentially salt-free puirified chymopapain solution to produce a dry, purified chymopapain of reduced immunogenicity and toxicity.

The present invention also comprises a purified chymopapain product of lower immunogenicity and toxicity produced by the above process.

The purified chymopapain of the present invention is further characterized by freedom from excessive odor and color. The method of the present invention may be carried out essentially continously since the carboxymethyl agarose gel exchange resin does not shrink in use and does not have to be removed from the column but may be merely treated with additional buffer solution to remove salts. This is contrasted with prior art resins such as carboxymethyl substituted dextran which shrinks in use, must be removed from the column, washed with water, allowed to re-swell, re-equilibrated with buffer, and then re-poured into the column for reuse.

The purified chymopapain of reduced immunogenicity made by the process of this invention, which is also essentially free of inactive components, is further characterized by its failure to form a precipitate in an acidified solution with barium chloride. This is in contrast with crude chymopapain which does form a precipitate under such conditions. While the reason why such precipitate forms with the unpurified chymopapain is not known, it has been determined that it is characteristic of crude chymopapain and particularly characteristic of the discarded portion of the chymopapain initially eluted from the exchanger in the process of the present invention which forms a precipitate with barium chloride after acidification.

OBJECTS OF THE INVENTION

One of the objects of the present invention is the provision of a method for producing a purified chymopapain having a minimum of colored, odorous, and non-proteolytic or inactive protein components.

A further object of the present invention is the provision of a process for producing an improved purified chymopapain which has a reduced toxic and/or anaphylactic effect when introduced and injected into mammalian systems.

A further object is the provision of a highly concentrated, but essentially completely proteolytic chymopapain fraction suitable for injection into mammalian systems.

A still further object is the provision of a method for making a purified chymopapain by the use of a carboxymethyl agarose gel column which does not shrink and does not have to be removed for reuse.

DESCRIPTION OF THE PREFERRED EMBODIMENTS

The crude chymopapain used as the starting material for the process of the present invention (from an ion exchange resin substrate) contains three sequentially elutable fractions of material that make up what is identified as crude chymopapain. They include a proteolytically inactive or active, colored, odorous component and two proteolytically active components herein called chymopapain I and II. It is obtained by the method of Jansen and Balls, J. Biol. Chem., Vol. 13, pp. 459-60 (1941). That method involves the treatment of a commercial papain concentrate by forming an aqueous acidic solution and saturating the solution with sodium chloride at a higher pH, decreasing the pH and thereafter dialyzing a solution of the crude chymopapain to produce a salt-free solution thereof, followed by lyophilizing of the solution to obtain a crude dry chymopain product.

The process of the present invention uses as a starting material the crude chymopapain produced by the method of Jansen and Balls but also can include other crude chymopapains.

The crude, chymopapain may be purified to remove inactive, colored, odoriferous and immunogenic components by the process of the present invention as shown in the following example.

EXAMPLE 1

All steps are performed at refrigerator temperatures. (2°-8° C.).

A. Crude chymopapain (about 29 g) were dissolved in 190 ml of pH 7.4 sodium phosphate buffer to give a 5% (W/V) solution.

B. The solution of crude chymopapain in buffer was added to a column of carboxymethyl agarose gel resin approximately 1.7 liters in volume (5×80 cm. approximate bed dimensions), which previously has been equilibrated with 0.05 M sodium phosphate buffer.

C. A gradient of NaCl in 0.05 M sodium phosphate buffer, pH 7.4 was then applied to the inlet of the column, such that the sodium chloride concentration increased in a linear fashion from 0 to 1.0 M with volume. The gradient was so arranged that when about 4.6 liters had been admitted to the column the incoming sodium chloride concentration was one molar.

D. The column effluent was collected with the aid of a drop counter in fractions of 25 mls in test tubes over about 40 hours.

E. The protein content and activity of each fraction were analyzed. Total protein by the biuret test was performed on 0.5 ml samples; activity was estimated by determining hydrolysis of DL-α-benzoyl-arginine-p-nitroanlide with 0.05 ml samples by the method of Erlanger, (Arch. Biochim. Biophys. 95, 271–78 (1961) adapted for use with chymopapain. A plot was made of the relative protein content against serially collected fractions. The protein content is conveniently measured by adding 0.5 ml of each fraction to 5 ml of biuret reagent, and determining the absorbance (A) at 540 nm ($A_{540}$) after 15 minutes. (See. FIG. 1 of the attached drawing).

F. The fractions containing the protein component which first eluted (along with deep brown colored components) from the column at sodium chloride concentrations of from zero to about 0.4 molar were discarded.

G. The remaining fractions recovered at concentration of from 0.4 to 1 molar were combined and dialyzed against several changes of distilled water at 2°-8° C. to remove sodium chloride and dissolved buffer.

H. The desalted product was then adjusted with 1 N NaOH to a pH of 6 and then freeze-dried to yield approximately 16.3 g of "chymopapain (purified)".

Reference is made to the attached drawing which is a graphic plot of protein content by the biuret test absorbance (A) at 540 nm ($A_{540}$) of the serially collected fractions of eluent from the column (left hand vertical axis) against the volume (in milliliters) of eluent collected (horizontal axis). Also included in the same graph as a broken line is the NaCl or salt concentration (right hand vertical axis) in terms of NaCl molarity of from zero to 1 molar on a linear gradient, plotted against the eluent volume as shown. The enzyme activity of the eluent, determined by the Erlanger method [absorbance at 410 nm ($A_{410}$)] is plotted as a broken line " - - - - " (right hand vertical axis) against eluent volume.

The first protein component was eluted from the column at sodium chloride molarities of from about zero to about 0.25 to 0.4 molar. It is characterized as a highly colored, odorous fraction and identified in the drawing as peak A. This component is discarded. The protein identified as peak A is frequently proteolytically inactive and contains most of the color elements found in the crude chymopapain. This protein fraction "A" is also characterized as forming a precipitate with barium chloride solution.

Subsequent fractions of purified chymopapain eluent comprise two additional and major peaks at sodium chloride concentrations of from 0.4 to 1 molar, which are identified as chymopapain I and II. Chymopapain I and II, recovered from the column are always proteolytically active and moreover do not form a precipitate with barium chloride solution in acid solution.

The crude chymopapain containing the proteolytically inactive protein component and the two proteolytically active components chymopapains I and II absorbed in the column are eluted with the salt-buffer solution at a pH of about 6.5 to 7.5, preferably at a pH of from 7.3 to 7.5.

The initial material (Peak A) eluted from the column is of variable enzyme activity, constituted about 15% by weight of the total material and was eluted at salt (NaCl) concentrations from zero up to about 0.25 to 0.4 molar.

The remainder of the eluent contains the proteolytically active components chymopapain I and II which are eluted and recovered from the column at salt concentrations from about 0.25 to 0.4 up to 1 molar. These two characteristic major peaks or protein constituents which make up about 85% of the total material are eluted and collected, at salt concentrations of from about 0.5 and 0.8 molar as may be seen in the drawing.

The absorption and elution process described above is carried out at refrigerator temperatures of from about 2°–8° C. The eluent fractions collected containing chymopapain I and II are combined and dialyzed against water to remove salt, as well as soluble buffer components, filtered and sterilized. The salt-free solution of essentially pure, proteolytically active chymopapain (I and II) is then lyophilized. The total yield is about 50-60% based on crude starting material. Although some inactive material is removed, the activity per unit weight of the final product is not increased, probably because of enzyme (activity) lost during processing.

While the crude chymopapain heretofore used in the treatment of abnormal or herniated discs behaves in tests as a mixture of protein fractions, the process of the present invention has removed a fraction of that protein (Peak A) which appears to be responsible for higher toxicity as observed in animal tests in which the two materials are compared.

As noted herein the purified chymopapain of the present invention may be distinguished from that of the prior art treatment with barium chloride in acid solution (HCl). Formation of a precipitate with barium choride is characteristic of the prior art crude (or toxic) chymopapain whereas the purified chymopapain of the present invention does not form a precipitate.

The following example illustrates the barium chloride test procedure used to distinguish the two chymopapain materials:

EXAMPLE 2

A 10% (w/v) aqueous solution of the chymopapain specimen was acidified with 1 ml of 1 N HCl to which was added 1 ml of 12% (w/v) barium chloride ($BaCl_2$) (prepared as a U.S.P. test solution (U.S. Pharmacopeia XX, p. 1103: 12 gm. of $BaCl_2$ to make 100 ml in distilled water). The following results were obtained:

| Crude Chymopapain | Result |
| --- | --- |
| Run A | moderate to heavy precipitate |
| Run B | moderate precipitate |
| Run C | moderate precipitate |
| Run D | moderate to heavy precipitate |

| Purified Chymopapain of the present invention | Result |
| --- | --- |
| Run E | clear |
| Run F | clear |
| Run G | essentially clear (slight haze) |
| Run H | clear |

The purified chymopapain of the present invention is also characterized by having a reduced color and odor as compared to the crude chymopapain starting material. The color factors in the crude chymopapain are associated with the first fraction of the chymopapain eluted from the chromatographic column which also has been found to form a precipitate with barium chloride solution as noted above. This precipitable fraction apparently is associated with most of the color and odor in the crude chymopapain and with the toxicity of crude chymopapain in mammals.

Accordingly, the reduced or minimal color of the purified chymopapain products of the present invention together with their failure to form a precipitate with barium chloride solution under acid conditions, may be taken as a measure of their freedom from the components or fractions which carry with them a higher risk of toxicity and are believed to be responsible in large part for the anaphylactic reactions that have been found to occur in a small number of mammalian subjects heretofore injected with the crude chymopapains used for this purpose.

As previously indicated above, the fractions of the chymopapain discarded in the process of the present invention, are in most instances essentially proteolytically inactive. This observation however, has been found to have exceptions in the case of certain crude chymopapain materials from India and Zaire. In chymopapains from other sources it has been found that this first fraction eluted in the process of the present invention does have some proteolytic activity, although of a low level. This aspect is significant because, depending on the source of the papain from which crude chymopapain is manufactured, the crude chymopapain may have two or three active components. This characteristic of the crude chymopapain now used for human disc therapy in Canada is not controlled and is a source of uncontrolled variability in a drug product. By purifying chymopapain to two active components a consistent product of lower toxicity is produced. The improved properties of the purified chymopapain produced by the method disclosed herein are shown in the reduced toxicity of that product in biological tests shown in the following.

INTRAVENOUS ACUTE TOXICITY

Actue intravenous toxicity tests were carried out to compare the chymopapain of the prior art purchased commercially in Canada (original source Baxter Travenol Laboratories) (herein called compound A) with the purified chymopapain of the present invention, (herein compound B), and a control, sterile water (compound C) by intravenous injection in various test animals. The compound B preparation was prepared in the laboratory by the process of the present invention from a lyophilized dosage unit form containing 23.0 milligrams of purified chymopapain and 3.5 milligrams of sodium cysteinate hydrochloride by the method described in the application of W. S. Smith, Ser. No. 263,197 of even date herewith incorporated herein by reference. Compound A contained about 27 mg of crude chymopapain, 0.37 mg. of disodium EDTA, and 3.5 mg of sodium cysteinate hydrocholoride.

Test 1 (mice)

Ten young adult mice (five male and five female) of the CD-1 strain were each injected intravenously with 0.01 ml/g (equivalent to 20,000 and 23,000 units/kg of body weight) of the test compounds A and B respectively in aqueous solutions having concentrations of 2,000 and 2,300 units/ml. The injection-site chosen was a lateral tail vein and the rate of injection with 1 milliliter per 30 seconds. The mice were observed at 2½ and 4 hours following dosing and twice daily (a.m. and p.m.) thereafter for a total period of 14 days.

Four out of the ten mice treated with compound A died within four hours after receiving the injection. The tails of eight of the surviving mice injected with compound A showed signs of necrosis. Four of the ten mice injected with compound B died at 2 days (one male and one female) and 4 days (two males). One of the surviving mice showed signs of tail necrosis at the end of the test period. No deaths were observed in mice injected with the control (compound C).

Test 2 (rabbits)

Three groups of four rabbits (two male, two female) were injected intravenously with 0.5 ml/kg body weight of the test compounds at dosage levels of 1,000 (compound A) and 1,150 (compound B) units per kg of body weight. Three of four rabbits (two male, one female) died within four hours after injection of Compound A. All of the rabbits injected with compound B survived as did the rabbits injected with the control (compound C).

In summary the tests demonstrated that the prior art chymopapain has a much higher toxicity risk than the purified chymopapain of the present invention.

REDUCED ALLERGENIC PROPERTIES (Guinea Pig Skin Sensitization)

A guinea pig dermal sensitization test was carried out on 32 male adult albino guinea pigs of the Hartley strain maintained in accordance with the Department of Health Education and Welfare Pub. No. 73-23 (N.I.H.) for 17 days prior to initiation of the study. The test animals were shaved 26-27 hours prior to testing to remove hair from the flank and back of each guinea pig. Any abnormality of skin (i.e., erythema, lesions) was a basis for rejection from the test as was any deviation in body weight. Thirty test animals were randomly selected from the screen group of 32. Compounds A and B as above-identified were formulated with sterile water to provide injection solutions. The concentration for compound A (commercial chymopapain) was 2,000 units/ml. The concentration for compound B (purified chymopapain) was 2,300 units/ml. A positive control, 2,4-dinitro-1-chlorobenzene was prepared as a 1.0% (W/V) solution identified as Compound D. A negative control (sterile water) was identified as compound C. Ten animals were used in each test group.

Sensitization tests were conducted by intradermal injection of the test and positive control compounds A, B and D on the right flank of the animals. Negative control injections (compound C, sterile water) was intradermally injected into the left flank of all test animals in the test groups. The test and controls were injected every other day three times per week until ten sensitizing doses had been administered. The initial volume injected was 0.05 and 0.10 ml on nine subsequent sensitizing doses.

Two weeks after the administration of the tenth sensitizing dose, a challenge dose of 0.05 ml of the test and control compounds were administered in the same manner as the sensitizing doses.

The animals were observed for mortality twice daily (a.m. and p.m.) for 37 days.

The following evaluation of skin lesions were made at 24 and 48 hours after injection and scored for intensity of erythema by measuring diameter (flare) and height of edema (wheal).

The following are the results of the average of the 24 and 48 hour observations.

|  | Diameter of Erythema* | Height of Edema* |
|---|---|---|
| Compound A | 14.8mm | 2.27 |
| Compound B | 9.9mm | 1.73 |
| Compound D (positive control) | 11.06mm | 2.71 |

*average of ten animals except in the case of compound D where two animals died (average of eight)

The results indicate that the commercially available crude chymopapain formulation has significantly greater sensitization liability than purified chymopapain of the present invention. Compound A had greater sensitization liability than that of positive control (D), 2,4-dinitro-1-chlorobenzene, a known sensitizer. Statistical analysis indicate differences between compounds A and B were significant for erythema ($p \leq 0.025$) and edema ($p \leq 0.002$).

From the foregoing, it is evident that the purified chymopapain prepared by the process of the present invention is a new form of chymopapain which is significantly less toxic than the crude chymopapain of the prior art.

From the experience of other researchers, it is apparent that the new improved purified form of chymopapain of the present invention may be confidently used in the procedure for the treatment of abnormal, damaged, or herniated discs in mammalian subjects including man.

As noted above, the purified chymopapain may be prepared by the process of the present invention in an essentially continuous manner since the carboxymethyl substituted agarose gel resin does not shrink in volume during use and does not have to be removed from the column for regeneration by washing and re-equilibrating with buffer and re-swelling, as is required for ion exchange resins such as "Sephadex" CM-50 (a carboxymethyl substituted cross-linked dextran copolymer), followed by re-pouring into the column, a costly and time consuming process. To operate the process of this invention in an essentially continuous fashion, the column of carboxymethyl agarose gel is regenerated in situ merely by pouring additional buffer through the column which re-equilibrates the same ready for reuse in the process. There is no shrinkage of the resin nor is there any need for removal, washing or reswelling. Other non-shrinking resin supports suitable for use in this invention are acrylamide gel resins.

What is claimed is:

1. A process for the purification of crude chymopapain to produce a purified chymopapain of reduced toxicity comprising:
    (a) contacting an aqueous buffered solution of crude chymopapain with a weakly acidic cationic exchanger comprising a column of carboxymethyl substituted cross-linked agarose gel, said exchanger having been previously equilibrated with aqueous buffer solution having a pH of between about 6.5 and 7.5;

(b) eluting the chymopapain retained on the exchanger with a similar aqueous buffer solution having a pH in the same pH as the buffer used for equilibrating the carboxymethyl substituted agarose gel, but having a linearly increasing ionic concentration of a compatible, non-reactive, water-soluble, pharmaceutically acceptable, neutral inorganic salt with respect to eluent volume;

(c) collecting and discarding a first series of fractions of eluent from said exchanger containing an initial protein component from crude chymopapain until the molarity of the eluent with respect to said soluble salt increases to and reaches the range of 0.25 to 0.4;

(d) continuously collecting and retaining a further series of fractions of chymopapain eluted from the exchanger comprising two proteolytically active chymopapain components at increasing soluble salt concentrations greater than about 0.25 to 0.4 molar, until substantially all of the said absorbed cymopapain is recovered;

(e) treating said retained fractions containing proteolytically active components of the chymopapain to remove the dissolved ionic inorganic salts, and buffer components; and (f) lyophilizing the essentially salt-free chymopapain solution to produce a dry, purified proteolytically active chymopapain essentially free of proteolytically inactive or toxic components.

2. The process according to claim 1 wherein the eluent buffer solution employed contains a water-soluble inorganic salt concentration gradient of from zero to 1 molar.

3. The process according to claim 1 wherein the pH of the exchanger is equilibrated to between 7.3 and about 7.5.

4. The process according to claim 1 wherein the aqueous solution of crude chymopapain, the buffer used to equilibrate the exchanger and the eluent are adjusted to a pH of about 7.4.

5. The process according to claim 1 wherein the water-soluble salt employed in the eluting solution is sodium chloride.

6. A process according to claim 1 wherein the soluble salt concentration in step (c) reaches a molarity of about 0.3.

7. A process according to claim 1 wherein the steps (a) through (d) are carried out at a temperature of from about 2° to 8° C.

8. A process according to claim 1 wherein the carboxymethyl substituted cross-linked agarose gel cationic exchanger have a neutralizing capacity of from about 0.02 to about 0.10 milliequivalents of sodium hydroxide/cc.

9. A process according to claim 1 wherein the purified chymopapain recovered is characterized by a failure to form a precipitate with acidified barium chloride solution.

10. A process according to claim 1 wherein the purified chymopapain is essentially free of colored materials.

11. A process according to claim 1 wherein the buffer solution used is a phosphate buffer.

12. A process according to claim 1 wherein a crude colored chymopapain is dissolved in a phosphate buffer at a concentration (weight to volume) of 12 to 18% and the buffer concentration with respect to phosphate is about 0.05 molar.

13. A process according to claim 1 wherein the soluble ionic inorganic salts are removed from the chymopapain solution in step (e) by dialysis.

14. A process according to claim 1 wherein step (e) also includes the steps of filtration and sterilization.

15. A process according to claim 1 wherein a sufficient amount of the colored protein component of the crude chymopapain initially eluted from the exchange is removed so that an acidified aqueous solution of the remainder of the proteolytically active chymopapain components eluted and recovered from said exchanger do not cause a precipitate when treated with barium chloride solution (USP).

16. A process according to claim 1 wherein the concentrations of salt in step (d) are gradually increased up to about 1 molar.

17. A process according to claim 16 wherein the purified chymopapain is recovered in the eluent fractions from the column at increasing salt concentrations of from about 0.3 to about 0.8 molar.

18. A process according to claim 17 wherein the purified chymopapain is essentially fully proteolytically active and is essentially free of colored, odoriferous and toxic antigens and is further characterized by its failure to form as precipitate with acidified barium chloride.

19. An essentially continuous method according to claim 1 wherein after the recovery of purified chymopapain from said eluent, residual salt is removed from the column by application thereto of salt-free buffer solution sufficient in volume to remove salt residual salt and equilibrate salt column and repeating the said process of claim 1.

20. A method of identifying a purified chymopapain essentially free of proteolytically inactive, antigenic and colored material, which comprises the essential absence of a precipitate formation of an acidified solution of said purified chymopapain when contacted with a U.S.P. test solution barium chloride.

* * * * *

UNITED STATES PATENT AND TRADEMARK OFFICE
CERTIFICATE OF CORRECTION

PATENT NO. : 4,374,926

DATED : February 22, 1983

INVENTOR(S) : Ivan J. Stern

Page 1 of 4

It is certified that error appears in the above-identified patent and that said Letters Patent is hereby corrected as shown below:

[56] OTHER PUBLICATIONS

Col. 2, line 22, "Shapiro Mutation Research, vol. 39, 149-1977). should be

-- Shapiro, Mutagen Research -- etc.

Col. 2, line 23, "Sussmuth et al., Mutation Research, vol. 40, 229-236 (1976)." should be -- Sussmuth et al., Mutagen Research, -- etc.

Col. 1, line 38, "sovlent" should be --solvent--

Col. 2, line 47, "puirified" should be -- purified--

Col. 6, line 47, "Actue" should be -- Acute --

Col. 7, line 38, "73-23" should be -- 78-23--

Col. 7, line 51, "1.0%" should be --0.1%--

Col. 8, line 51 "in situ" should be italicized
        -- in situ --

UNITED STATES PATENT AND TRADEMARK OFFICE
CERTIFICATE OF CORRECTION

PATENT NO. : 4,374,926

DATED : February 22, 1983

INVENTOR(S) : Ivan J. Stern

It is certified that error appears in the above-identified patent and that said Letters Patent is hereby corrected as shown below:

IN THE CLAIMS:

Col. 9, line 22, "cymopapain" should be --chymopapain--

Col. 10, line 46, "solution sufficient in volume to remove salt residual salt" should be -- solution sufficient in volume to remove said residual salt --

Col. 10, line 47, "and equilibrate salt column" etc. should be
-- and equilibrate said column --

UNITED STATES PATENT AND TRADEMARK OFFICE
CERTIFICATE OF CORRECTION

PATENT NO. : 4,374,926

DATED : February 22, 1983

INVENTOR(S) : Ivan J. Stern

Page 3 of 4

It is certified that error appears in the above-identified patent and that said Letters Patent is hereby corrected as shown below:

Col. 1, line 16, "J. Biol. Chem.," should be italicized
-- *J. Biol. Chem.,* --

Col. 1, ll. 32-33 "Abstracts of Papers of the 140th Meeting of the Am. Chem. Soc'y, Chicago," should be italicized -- *Abstracts of Papers of the 140th Meeting of the Am. Chem. Soc'y., Chicago,*

Col. 1, line 34 "J. Biol. Chem.," should be italicized
-- *J. Biol. Chem .,* --

Col. 1 ll. 35-36, "Biochim. Biophys. Acta," should be italicized
-- *Biochim. Biophys. Acta,* --

Col. 1, line 66, "methods i.e." should be
-- methods, i.e,

Col. 1, line 67, "Biochem. J." should be italicized
-- *Biochem. J.* --

Col. 2, line 56 "continously" should be -- continuously --

Col. 4, line 17, "nitroanlide" should be -- nitroanilide --

UNITED STATES PATENT AND TRADEMARK OFFICE
CERTIFICATE OF CORRECTION

PATENT NO. : 4,374,926

DATED : February 22, 1983

INVENTOR(S) : Ivan J. Stern

It is certified that error appears in the above-identified patent and that said Letters Patent is hereby corrected as shown below:

Col. 4, line 18, "(Arch. Biochim. Biophys. 95, 271-78 (1961)" should be enclosed by brackets
-- [Arch. Biochim. Biophys. 95, 271-78 (1961)]

Col. 5, line 52 "(prepared as a U.S.P. test solution (U.S. Pharmacopeia XX, p. 1103: 12 gm. of $BaCl_2$ to make 100 ml in distilled water)." should be -- prepared as a U.S. P. test solution --

Signed and Sealed this

Sixth Day of December 1983

[SEAL]

Attest:

Attesting Officer

GERALD J. MOSSINGHOFF

Commissioner of Patents and Trademarks